US010011863B2

(12) United States Patent
Lipsky et al.

(10) Patent No.: US 10,011,863 B2
(45) Date of Patent: Jul. 3, 2018

(54) METHODS FOR DETECTING ENHANCED NMDA RECEPTOR FUNCTION AND USES THEREOF

(71) Applicant: INOVA HEALTH SYSTEM, Falls Church, VA (US)

(72) Inventors: Robert H. Lipsky, Kensington, MD (US); Mingkuan Lin, Fairfax, VA (US); Yang Jiang, Lexington, KY (US)

(73) Assignee: INOVA HEALTH SYSTEM, Falls Church, VA (US)

( * ) Notice: Subject to any disclaimer, the term of this patent is extended or adjusted under 35 U.S.C. 154(b) by 0 days.

(21) Appl. No.: 15/589,257

(22) Filed: May 8, 2017

(65) Prior Publication Data

US 2017/0349943 A1    Dec. 7, 2017

Related U.S. Application Data

(60) Provisional application No. 62/341,883, filed on May 26, 2016.

(51) Int. Cl.
*C07H 21/04* (2006.01)
*C12Q 1/68* (2018.01)
*C12Q 1/6837* (2018.01)

(52) U.S. Cl.
CPC ..... *C12Q 1/6837* (2013.01); *C12Q 2600/156* (2013.01)

(58) Field of Classification Search
None
See application file for complete search history.

(56) References Cited

U.S. PATENT DOCUMENTS

2007/0048767 A1    3/2007  Martucci et al.
2009/0253585 A1   10/2009  Diatchenko et al.

OTHER PUBLICATIONS

Syvanen (Nature, vol. 2, pp. 930-942, Dec. 2001). (Year: 2001).*
Grafman, Vietnam Head Injury Study, Aug. 2007 (Year: 2007).*
Lipsky et al. (2011-2012 ARDRAF Final ProjectReport, abstract). (Year: 2011).*
Ioannidis (Nature Genetics, vol. 29, pp. 306-309, Nov. 2001) (Year: 2001).*
Hirschhorn et al. (Genetics in Medicine. vol. 4, No. 2, pp. 45-61, Mar. 2002) (Year: 2002).*
dbSNP, ss4950068, https://www.ncbi.nlm.nih.gov/projects/SNP/snp_ss.cgi?subsnp_id=4950068 (Year: 2001).*
Lipsky, Robert H., 'Functional Characterization of Promoter Po Lymor-Ph I Sms of the Human Grin2b Glutamate Receptor Gene Associated With Altered Memory Functioning in Older Adults' In: 2011-2012 Ardraf Final Project Report, 2012, 2 Page See p. 2, 2nd Paragraph.
Lipsky, Robert H., 'Understanding the Development of Alzheimer's Disease From the Perspective of the Aging Brain' In: George Mason University College of Science Biology Department Seminar Fall 2015, Oct. 20, 2015, Johnson Center Room, 1st Sheet See 1st Sheet.
Yoo, Hee Jeong et al., 'Family Based Association of Grin2a and Grin2b With Korean Autism Spectrum Disorders' Neuroscience Letters. 2012, vol. 512, pp. 89-93 Scc Abstract; Supplement Table 2.
Andreoli, Virginia et al., 'Potential Involvement of Grin2b Encoding the Nmda Receptor Subunit Nr2b in the Spectrum of Alzheimer's Disease', Journal of Neural Transmission, 2014, vol. 121, pp. 533-542 See the Whole Document.
Jiang, Yang et al., 'Functional Human Grin2b Promoter Polymorphism and Variation of Mental Processing Speed in Older Adults', Aging (Albany Ny), Epub. Apr. 24, 2017, vol. 9, No. 4, pp. 1293-1305 See Abstract; p. 1294, Right Column, 2nd-4th Paragraphs; p. 1296, Right Column; p. 1299, Left Column, 3rd Paragraph; p. 1300, Right Column, 3rd.
International Search Report of PCT/US2017/031540 dated Aug. 8, 2017.
Lipsky H. Robert; "Understanding the Development of Alzheimer's Disease from the Perspective of the Aging Brain", George Mason University, College of Science, Biology Department Seminar, Fall 2015.

* cited by examiner

*Primary Examiner* — Jeanine A Goldberg
(74) *Attorney, Agent, or Firm* — Polsinelli PC

(57) ABSTRACT

A method of determining the risk of cognitive decline in an aging subject is provided. The method includes analyzing an MRNA transcript including a GRIN2B nucleic acid sequence for the presence of the A allele in a biological sample obtained from the subject. The method also includes identifying the subject as having a decreased risk of cognitive decline when the A allele is present.

8 Claims, 7 Drawing Sheets

METHODS FOR DETECTING ENHANCED NMDA RECEPTOR FUNCTION AND USES THEREOF

CROSS-REFERENCE TO RELATED APPLICATIONS

This application claims priority to U.S. Provisional Patent Application No. 62/341,883, which was filed in the U.S. Patent and Trademark Office on May 26, 2016, all of which is incorporated herein by reference in its entirety for all purposes.

The instant application contains a Sequence Listing which has been submitted in ASCII format via EFS-Web and is hereby incorporated by reference in its entirety.The Sequence Listing is being concurrently submitted via EFS-Web as an ASCII text file named 084453 569289 Sequence Listing.Txt,created Jun. 8,2017.

GOVERNMENTAL RIGHTS

This invention was made with government support under grants P30 AG028383 and K01 AG000986 awarded by NIH. The government has certain rights in the invention.

FIELD OF THE INVENTION

The disclosure provides methods for predicting memory performance and determining the risk for cognitive decline.

BACKGROUND OF THE INVENTION

The earliest and the most severe memory loss in old age and dementia occur in recent memory and working memory. Compared to young adults, older adults exhibit deficits in working memory, an online memory mechanism that allows manipulation of a current target image amongst distracting stimuli. Remote memory or long-term is better retained. Evidence from neuropsychological and neuroimaging studies of visual working memory indicates that working memory relies on activation of the ventral temporal cortex, and top-down feedback from the prefrontal and medial temporal cortex, and the hippocampus. It has been observed that there are significant individual differences in cognitive aging among healthy cognitively intact older adults due to genetic, learning and environmental factors. Since genetic factors influence working memory performance in the aging brain and the exact underlying mechanisms are not well understood, there is a need in the art to identify genetic polymorphisms critical to the molecular foundation of learning and memory in individuals' brain processing speed and cortical responses during a working memory task.

BRIEF DESCRIPTION OF THE FIGURES

The application file contains at least one drawing executed in color. Copies of this patent application publication with color drawing(s) will be provided by the Office upon request and payment of the necessary fee.

DETAILED DESCRIPTION OF THE INVENTION

Figure 1:
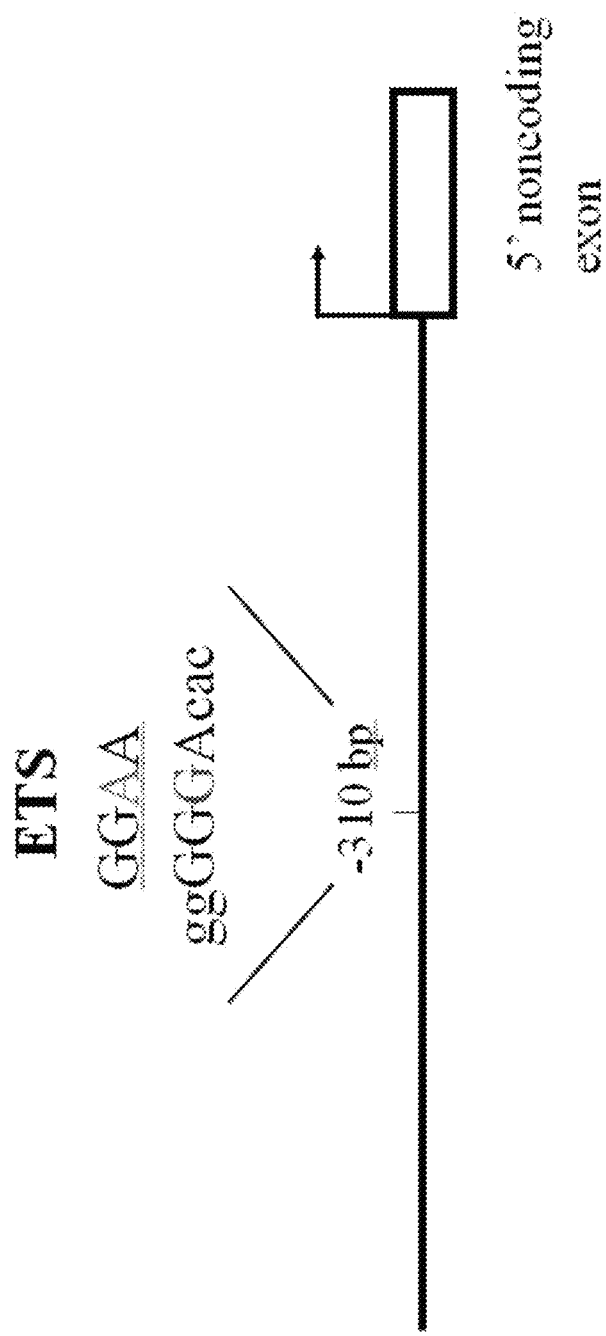
FIG. 1 depicts a schematic showing that the A allele of SNP rs3764030 creates an E twenty-six (ETS) transcription factor binding site in the promoter region of the human GRIN2B (GRIN2B gene in italics) gene, which encodes the GluN2B subunit of the N-methyl-D-aspartate (NMDA) receptor.

Described herein is the discovery that a G>A single nucleotide polymorphism (SNP rs3764030) that is 310 bps upstream of the transcription start site for the human GRIN2B gene promoter creates an E-twenty six (ETS) transcription factor binding site. Accordingly, this disclosure is the first report that SNP rs3764030, which results in the A allele, affects GRIN2B mRNA levels. An association of this gain-of-function SNP in the GRIN2B gene and memory performance in a normally aged population of adults was demonstrated. Accordingly, SNP rs3764030 within the promoter of the GRIN2B gene could be used to predict brain responses and memory performance during working memory. Further, it was shown that older subjects with the A allele performed better than those without the allele. This data suggests that enhancing levels of GRIN2B protein during aging protects subjects from memory loss in later years. Additionally, predicting a subject's memory performance during aging by assessing for the presence of the A allele (SNP rs3764030) allows for earlier intervention thereby slowing the progression of aging effects on the brain.

Various aspects of the disclosure are described in more detail below.

I. Methods of Detection

In an aspect, the disclosure provides a method to classify a subject based on the presence of the GRIN2B A allele in a biological sample obtained from the subject. The method generally comprises: (a) analyzing GRIN2B nucleic acid for the presence of the A allele; and (b) classifying the subject as having the A allele if GGAA is detected about 310 base pairs upstream of the transcription start site for GRIN2B. The subject may be classified as having the A allele if they are either homozygous for the A allele or heterozygous for the A allele. A subject homozygous for the A allele has only has the GGAA sequence about 310 base pairs upstream of the transcription start site for GRIN2B, and may be referred to as A/A. A subject heterozygous for the A allele has the GGAA sequence about 310 base pairs upstream of the transcription start site for GRIN2B and a GGGA sequence about 310 base pairs upstream of the transcription start site for GRIN2B, and may be referred to as A/G. A skilled artisan would be able to determine the transcription start site for GRIN2B. More specifically, a subject has the A allele if the SNP rs3764030 is detected. SNP rs3764030 is located on chromosome 12 at position 13980398. The sequence information for rs3764030 may be found at ncbi.nlm.nih.gov/SNP/snp_ref.cgi?rs=rs3764030. As used herein, "GRIN2B" refers to the human form of nucleic acid that encodes for the glutamate [NMDA] receptor subunit GluN2B or epsilon-2 protein. The glutamate [NMDA] receptor subunit epsilon-2 protein may also be referred to as N-methyl D-aspartate receptor subtype 2B, GRIN2B, NMDAR2B, GluN2B, or NR2B. Other suitable terms for GRIN2B include EIEE27, GluN2B, MRD6, NMDAR2B, NR2B, and hNR3. As used herein, the "A allele" refers to a sequence of GRIN2B comprising GGAA about 310 base pairs upstream of the transcription start site for GRIN2B. The "A allele" also refers to SNP rs3764030.

In another aspect, the disclosure provides a method of predicting memory performance in a subject. The method comprises: (a) analyzing GRIN2B nucleic acid for the presence of the A allele in a biological sample obtained from the subject; and (b) identifying the subject as having improved memory performance 1 or more years following analysis relative to a reference value when the A allele is present. In an embodiment, the reference value is memory performance in a subject of the same age without the A allele. In another embodiment, the reference value is a standard value associated with the memory performance of a group of subjects of the same age without the A allele. The subject is predicted to have improved memory performance relative to a reference value 1 or more years following the detection of the A allele. For example, the subject is predicted to have improved memory performance relative to a reference value about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 25 years, about 30 years, about 35 years, about 40 years, about 45 years, about 50 years, or more than 50 years following the detection of the A allele. Memory performance may be measured by measuring sensory memory, short-term memory (also referred to as working memory), and/or long-term memory. Long term memory includes explicit memories (conscious) and implicit memories (unconscious). Explicit memory includes declarative memory which includes episodic memory and semantic memory. Implicit memory includes procedural memory. Any of the aforementioned types of memory may be used to measure memory performance. In a specific embodiment, short-term memory (also known as working memory) may be used to measure memory performance. Methods of measuring memory performance are known in the art. Non-limiting examples of methods of measuring memory performance include measuring reaction time, measuring accuracy of behavioral responses, and measuring recall. Numerous tests are known to measure memory including the reading span task, the operation spank task, the rotation spank task, the verbal updating task, the numerical updating task, the spatial-figural updating task, the recall 1-back task, binding tasks, secondary memory tasks, and reasoning tasks. Specifically, the methods described in the Examples may be used to measure memory performance.

In still another aspect, the disclosure provides a method of predicting reaction time in a subject. The method comprises: (a) analyzing GRIN2B nucleic acid for the presence of the A allele in a biological sample obtained from the subject; and (b) identifying the subject as having improved reaction time 1 or more years following analysis relative to a reference value when the A allele is present. In an embodiment, the reference value is reaction time in a subject of the same age without the A allele. In another embodiment, the reference value is a standard value associated with the reaction time of a group of subjects of the same age without the A allele. The subject is predicted to have improved reaction time relative to a reference value 1 or more years following the detection of the A allele. For example, the subject is predicted to have improved reaction time relative to a reference value about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 25 years, about 30 years, about 35 years, about 40 years, about 45 years, about 50 years, or more than 50 years following the detection of the A allele. Methods of measuring reaction time are known in the art. Specifically, reaction time may be measured as described in the Examples.

In still yet another aspect, the disclosure provides a method of determining the risk of cognitive decline in an aging subject. The method comprises: (a) analyzing GRIN2B nucleic acid for the presence of the A allele in a biological sample obtained from the subject; and (b) identifying the subject as having a decreased risk of cognitive decline when the A allele is present. As used herein, "cognitive decline" refers to an impairment of cognition or memory that represents a deterioration from a previous level of function. Non-limiting examples of measures of cognitive decline include memory, reaction time, learning, thinking, language, judgment, decision-making, and motor coordination. Diseases or disorders associated with cognitive decline include dementia, Alzheimer's disease, delirium, and amnesia. Accordingly, the disclosure also provides a method of determining the risk of dementia in an aging subject comprising: (a) analyzing GRIN2B nucleic acid for the presence of the A allele in a biological sample obtained from the subject; and (b) identifying the subject as having a decreased risk of dementia when the A allele is present. As used herein, an "aging subject" is a subject 30 years or more. For example, the subject may be 30 years or more, 35 years or more, 40 years or more, 45 years or more, 50 years or more, 55 years or more, 60 years or more, 65 years or more, 70 years or more, 75 years or more, 80 years or more, 85 years or more, 90 years or more, 95 years or more, or 100 years or more. In an embodiment, the method further comprises treating a subject if the A allele is absent. Non-limiting examples of treatment include drugs to boost neurotransmitter levels (e.g., Aricept, Razadyne and Exelon), drugs to regulated the activity of the neurotransmitter glutamate (e.g., memantine), occupational therapy, environmental approaches (e.g., reduce clutter and/or noise), donepezil, vitamin E, diet and exercise, and cognitive rehabilitation.

In other aspects, the disclosure provides a method of determining treatment of an aging subject. The method comprises: (a) analyzing GRIN2B nucleic acid for the presence of the A allele in a biological sample obtained from the subject; (b) classifying the subject as having the A allele if GGAA is detected about 310 base pairs upstream of the transcription start site for GRIN2B or not having the A allele if GGGA is detected about 310 base pairs upstream of the transcription start site for GRIN2B; and (c) treating the subject if the A allele is not detected. The absence of the A allele may be indicative of cognitive decline upon aging. For example, the absence of the A allele may be indicative of declines in memory upon aging. Further, the absence of the A allele may be indicative of dementia upon aging. Accordingly, if the A allele is not detected, the subject may be more aggressively treated relative to a subject possessing the A allele. Non-limiting examples of treatment for memory decline, cognitive decline and/or dementia include drugs to boost neurotransmitter levels (e.g., Aricept, Razadyne and Exelon), drugs to regulated the activity of the neurotransmitter glutamate (e.g., memantine), occupational therapy, environmental approaches (e.g., reduce clutter and/or noise), donepezil, vitamin E, diet and exercise, and cognitive rehabilitation.

In any of the foregoing embodiments, the subject may or may not be diagnosed with cognitive decline, memory loss and/or dementia. In certain embodiments, the subject may not be diagnosed with cognitive decline, memory loss and/or dementia but is suspected of having cognitive decline, memory loss and/or dementia based on symptoms. Non-limiting examples of symptoms of cognitive decline, memory loss and/or dementia that may lead to a diagnosis include confusion, poor motor coordination, loss of short-term or long-term memory, identity confusion, impaired judgment, emotional outbursts, isolation, and/or dulled or nonexistent emotions. In other embodiments, the subject may not be diagnosed with cognitive decline, memory loss and/or dementia but is at risk of having cognitive decline, memory loss and/or dementia. Non-limiting examples of risk factors for cognitive decline, memory loss and/or dementia include family history, aging, cardiovascular disease, diabetes, smoking, depression, high blood pressure, elevated cholesterol, lack of physical exercise, and infrequent participation in mentally or socially stimulating activities. In other embodiments, the subject has no symptoms and/or no risk factors for cognitive decline, memory loss and/or dementia. Methods of diagnosing cognitive decline, memory loss and/or dementia are known in the art. Non-limiting examples of method of diagnosing cognitive decline, memory loss and/or dementia include a thorough medical history, neurological exam to test reflexes, eye movements and/or walking and balance, blood tests, brain imaging, and/or mental status testing.

Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In an embodiment, the animal is a laboratory animal. Non-limiting examples of a laboratory animal may include rodents, canines, felines, and non-human primates. In certain embodiments, the animal is a rodent. In a preferred embodiment, the subject is human.

The human subject may be of any age. However, since cognitive decline is normally associated with aging, a human subject may be an older human subject. In some embodiments, the human subject may be about 30, 35, 40, 45, 50, 55, 60, 65, 70, 75, 80, 85, 90, 95 years of age or older. In some preferred embodiments, the human subject is 30 years of age or older. In other preferred embodiments, the human subject is 40 years of age or older. In other preferred embodiments, the human subject is 45 years of age or older. In yet other preferred embodiments, the human subject is 50 years of age or older. In still other preferred embodiments, the human subject is 55 years of age or older. In other preferred embodiments, the human subject is 60 years of age or older. In yet other preferred embodiments, the human subject is 65 years of age or older. In still other preferred embodiments, the human subject is 70 years of age or older. In other preferred embodiments, the human subject is 75 years of age or older. In still other preferred embodiments, the human subject is 80 years of age or older. In yet other preferred embodiments, the human subject is 85 years of age or older. In still other preferred embodiments, the human subject is 90 years of age or older.

(a) Biological Sample

As used herein, the term "biological sample" refers to a sample obtained from a human subject. Any biological sample containing GRIN2B nucleic acid is suitable. Numerous types of biological samples are known in the art. Suitable biological sample may include, but are not limited to, tissue samples or bodily fluids. In some embodiments, the biological sample is a tissue sample such as a tissue biopsy. The biopsied tissue may be fixed, embedded in paraffin or plastic, and sectioned, or the biopsied tissue may be frozen and cryosectioned. In other embodiments, the sample may be a bodily fluid. Non-limiting examples of suitable bodily fluids include blood, plasma, serum, peripheral blood, bone marrow, urine, saliva, sputum, and cerebrospinal fluid. In a specific embodiment, the biological sample is blood, plasma, serum. In another specific embodiment, the biological sample is blood. The fluid may be used "as is", the cellular components may be isolated from the fluid, or a nucleic acid fraction may be isolated from the fluid using standard techniques.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that GRIN2B can be accurately detected.

(b) Analyzing GRIN2B Nucleic Acid

Typically, analyzing GRIN2B nucleic acid may comprise identifying the presence of the A allele. As used herein, the "A allele" refers to a sequence of GRIN2B comprising GGAA about 310 base pairs upstream of the transcription start site for GRIN2B. The "A allele" also refers to SNP rs3764030. The sequence surrounding SNP rs3764030 comprises SEQ ID NO:1

(CGCGTCAGTGTGCCCCTTCCAAGAAATGCCCAGTGTGCACCCCGTGCACA

ATCAGAACCCATTCAGCACAAGCCCGGGGTGGGAGGCGGCGCTGCTGCTGG

AGGCGATGGGGAGAGCGAGCGAGACAAGTCAGCAGCAATGCAGATGGGGCT

GGGGGCCGCACTCGCTGGCGAGTTAAGTGGGAATTGTGTTTCTGCGTGTGT

GTGAGTGTGTGTTGCTGTATGGTGCCGCTTCTCCCCCCCTTCCTCCTTCCT

TCCCACTTCCCTCCTTCGCTCGCTCCCTCCCTCTCTCCTCTTCCATTCAGG

TTGGCTTTCCCACCTCTCATCCGTGCCTGTCCCAGGAATGGTATAGCCAGA

CCTTTTCTGAATTATTTATAGACCGGTACCAGCTGTTTTCAATTCCTCTCG

TGTGCACTCTGTGGGAAATGCGGGGTTTCCTCCCCCCTTTCCTTAAAACGA

ATTGATATCTTTTTCGGAATGCATTTTTCTCACCCTCCGGGGRACACGCGA

ATCAAGCCCTGACCGCCTCTTTTTCCCCCTTAGGAAGGGGACGCTTTGGGA

ATGACCATGCTCCACCGAGGGACGGAGCCGGCCCCCAGCTTCTCCACACAG

AGCCTCCTCCACTAACGCTCCAAAAACCAAAAACCGTAATTGCCAGAAGAA

GCGTTAAAAATCTATTCCAGCCACTAACCTCACATGCACACGGAATAATTA

CTCTGGATTCTGCATTGTGAGCTGCTCTCCATACCCTGAATTACCTTTGAA

TTAAATCTTTTTTTTTTGAATTTGCATCTCTTCAAGACACAAGATTAAAA

CAAAATTTACGCTAAATTGGATTTTAAATTATCTTCCGTTCATTTATCCTT

CGTCTTTCTTATGTGGATATGCAAGCGAGAAGAAGGGACTGGACATTCCCA

ACATGCTCACTCCCTTAATCTGTCCGTCTAGAGGTTTGGCTTCTACAAACC

AAGGTAGGGCAAATTCTATTTTATTTTTTCCTC), wherein R indicates the single nucleotide polymorphism where the nucleotide is either an A or a G.

The A allele creates an E twenty-six (ETS) transcription factor binding site in the promoter region of the human GRIN2B nucleic acid. The binding of an ETS transcription factor increases the expression of GRIN2B mRNA, synthesis of GRIN2B protein, or activity of GRIN2B protein when compared to a sequence of GRIN2B gene without the A allele. The presence of the A allele may be identified using methods commonly known in the art. Generally speaking, all or a portion of the promoter region upstream of the GRIN2B nucleic acid sequence may be sequenced and compared to SNP rs3764030 (SEQ ID NO:1) to identify the A allele.

With the knowledge of the sequence of the A allele provided herein, it is a routine matter to design detection means such as primers and/or probes that would be able to detect and/or identify the A allele. Possible techniques which might be utilized are well-established in the prior art and their use is readily adaptable by the skilled person for the purposes of detecting the GRIN2B A allele disclosed herein. For example, amplification techniques may be used. Non-limiting examples of amplification techniques may include polymerase chain reaction, ligase chain reaction, nucleic acid sequence based amplification (NASBA), strand displacement amplification (SDA), transcription mediated amplification (TMA), Loop-Mediated Isothermal Amplification (LAMP), Q-beta replicase, Rolling circle amplification, 3SR, ramification amplification (Zhang et al. (2001) Molecular Diagnosis 6 p 141-150), multiplex ligation-dependent probe amplification (Schouten et al. (2002) Nucl. Ac. Res. 30 e57). Other related techniques for detecting mutations such as SNPs may include restriction fragment length polymorphism (RFLP), single strand conformation polymorphism (SSCP) and denaturing high performance liquid chromatography (DHPLC). A summary of many of these techniques can be found in "DNA Amplification: Current technologies and applications" (Eds. Demidov & Broude (2004) Pub. Horizon Bioscience, ISBN:0-9545232-9-6) and other current textbooks.

Alternatively, probe based techniques may be used to detect the A allele. For example, a nucleic acid probe that is complementary or hybridizable to the A allele may be used. The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence (e.g. the A allele). The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length. In some embodiments, a probe comprises about 5, about 10, about 15, about 20, about 25, about 30 bases upstream of the single nucleotide polymorphism (SNP) and about 5, about 10, about 15, about 20 about 35, about 30 bases downstream of the SNP. For example, a probe may comprise the sequence set forth in SEQ ID NO:6 (CATCTC-CGGGGAACACGCGAA). The probe may further comprise a label for detection of the presence of the A allele. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, Ni2+, Flag tags, myc tags, heavy metals, and enzymes (including alkaline phosphatase, peroxidase, and luciferase).

(c) Determining the Risk of Cognitive Decline

A method of the disclosure comprises determining the risk of cognitive decline. The level of risk is a measure of the probability of cognitive decline occurring in a given individual. As used herein, "cognitive decline" refers to an impairment of cognition or memory that represents a deterioration from a previous level of function. If the A allele is identified, as described above, in a sample from a subject, then the subject is at a lower risk (i.e., there is a decreased probability) of developing cognitive decline then a subject without the A allele. For instance, the risk may be less than about 5%, less than about 10%, less than about 15%, less than about 20%, less than about 25%, less than about 30%, less than about 35%, less than about 40%, less than about 45%, or less than about 50%.

Alternatively, if the A allele is not identified in a sample from a subject, then the subject is at a higher risk of developing cognitive decline. For instance, the risk may be greater than about 95%, greater than about 90%, greater than about 85%, greater than about 80%, greater than about 75%, greater than about 70%, greater than about 65%, greater than about 60%, greater than about 55%, or greater than about 50%.

Increased or decreased "risk" or "probability" may be determined, for example, by comparison to the average risk or probability of an individual subject developing cognitive decline within a defined population. In this theoretical context, an increased risk for an individual will mean that they are more than 50% likely to develop cognitive decline within 5 years, whereas a reduced risk will mean that they are less than 50% likely to develop cognitive decline.

II. Methods of Treatment

In a different aspect, the disclosure provides a method to enhance memory in a subject. The method comprises administering a composition comprising a compound that increases GRIN2B activity or expression. Memory enhancement may be measured by measuring memory performance at one point in them and then measuring memory performance at a later point in time, wherein when memory performance improves from the first point in time to the second point in time, memory is enhanced. Memory performance may be measured by measuring sensory memory, short-term memory (also referred to as working memory), and/or long-term memory. Long term memory includes explicit memories (conscious) and implicit memories (unconscious). Explicit memory includes declarative memory which includes episodic memory and semantic memory. Implicit memory includes procedural memory. Any of the aforementioned types of memory may be used to measure memory performance. In a specific embodiment, short-term memory (also known as working memory) may be used to measure memory performance. Methods of measuring memory performance are known in the art. Non-limiting examples of methods of measuring memory performance include measuring reaction time, measuring accuracy of behavioral responses, and measuring recall. Numerous tests are known to measure memory including the reading span task, the operation spank task, the rotation spank task, the verbal updating task, the numerical updating task, the spatial-figural updating task, the recall 1-back task, binding tasks, secondary memory tasks, and reasoning tasks. Specifically, the methods described in the Examples may be used to measure memory performance.

In another different aspect, the disclosure provides a method to protect against memory loss in a subject. The method comprises administering a composition comprising a compound that increases GRIN2B activity or expression. Measuring memory performance, as described above, may be used to measure memory loss.

In still another different aspect, the disclosure provides a method to delay the onset of cognitive decline in a subject. The method comprises administering a composition comprising a compound that increases GRIN2B activity or expression. As used herein, "cognitive decline" refers to an impairment of cognition or memory that represents a deterioration from a previous level of function. Non-limiting examples of measures of cognitive decline include memory, reaction time, learning, thinking, language, judgment, decision-making, and motor coordination. Diseases or disorders associated with cognitive decline include dementia, Alzheimer's disease, delirium, and amnesia. Accordingly, the disclosure also provides a method to delay the onset of dementia in a subject comprising administering a composition comprising a compound that increases GRIN2B activity or expression. For example, the onset of cognitive decline may be delayed about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 25 years, about 30 years, about 35 years, about 40 years, about 45 years, about 50 years, or more than 50 years following administration of a composition comprising a compound that increases GRIN2B activity or expression.

A subject may be as described above in Section I.

(a) Compositions

In an aspect, a composition comprises a compound that increases GRIN2B activity or expression. A composition may optionally comprise one or more additional drug or therapeutically active agent in addition to a compound that increases GRIN2B activity or expression. A composition may further comprise a pharmaceutically acceptable excipient, carrier or diluent. Further, a composition may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants.

Methods to determine if a compound increases GRIN2B activity or expression are known in the art. For example, GRIN2B nucleic acid expression, GRIN2B protein expression, or GRIN2B activity may be measured as described in more detail below.

A compound with the ability to increase GRIN2B activity or expression may potentially be used as a drug to prevent cognitive decline and/or improve memory. A compound may include, without limitation, a drug, a small molecule, a peptide, a nucleic acid molecule, a protein, an antibody, and combinations thereof. A nucleic acid molecule may be an antisense oligonucleotide, a ribozyme, a small nuclear RNA (snRNA), a long noncoding RNA (LncRNA), or a nucleic acid molecule which forms triple helical structures. In certain embodiments, a compound with the ability to increase GRIN2B activity or expression may be the GRIN2B nucleic acid. For example, an expression vector encoding the GRIN2B nucleic acid may be delivered to a cell using a viral vector or via a non-viral method of transfer. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. An expression construct encoding the GRIN2B nucleic acid that is introduced to the cell may be linear or circular, may be single-stranded or double-stranded, and may be DNA, RNA, or any modification or combination thereof.

i. GRIN2B Nucleic Acid Expression

In an embodiment, GRIN2B nucleic acid expression may be measured to identify a compound that increases GRIN2B. For example, when GRIN2B nucleic acid expression is increased in the presence of a compound relative to an untreated control, the compound increased GRIN2B. In a specific embodiment, GRIN2B mRNA may be measured to identify a compound that increased GRIN2B expression.

Methods for assessing an amount of nucleic acid expression in cells are well known in the art, and all suitable methods for assessing an amount of nucleic acid expression known to one of skill in the art are contemplated within the scope of the invention. The term "amount of nucleic acid expression" or "level of nucleic acid expression" as used herein refers to a measurable level of expression of the nucleic acids, such as, without limitation, the level of messenger RNA (mRNA) transcript expressed or a specific variant or other portion of the mRNA, the enzymatic or other activities of the nucleic acids, and the level of a specific metabolite. The term "nucleic acid" includes DNA and RNA and can be either double stranded or single stranded. Non-limiting examples of suitable methods to assess an amount of nucleic acid expression may include arrays, such as microarrays, polymerase chain reaction (PCR), such as RT-PCR (including quantitative RT-PCR), nuclease protection assays and Northern blot analyses. In a specific embodiment, determining the amount of expression of a target nucleic acid comprises, in part, measuring the level of target nucleic acid mRNA expression.

In one embodiment, the amount of nucleic acid expression may be determined by using an array, such as a microarray. Methods of using a nucleic acid microarray are well and widely known in the art. For example, a nucleic acid probe that is complementary or hybridizable to an expression product of a target gene may be used in the array. The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence. In one example, the probe hybridizes to an RNA product of the nucleic acid or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

In another embodiment, the amount of nucleic acid expression may be determined using PCR. Methods of PCR are well and widely known in the art, and may include quantitative PCR, semi-quantitative PCR, multiplex PCR, or any combination thereof. Specifically, the amount of nucleic acid expression may be determined using quantitative RT-PCR. Methods of performing quantitative RT-PCR are common in the art. In such an embodiment, the primers used for quantitative RT-PCR may comprise a forward and reverse primer for a target gene. The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

The amount of nucleic acid expression may be measured by measuring an entire mRNA transcript for a nucleic acid sequence, or measuring a portion of the mRNA transcript for a nucleic acid sequence. For instance, if a nucleic acid array is utilized to measure the amount of mRNA expression, the array may comprise a probe for a portion of the mRNA of the nucleic acid sequence of interest, or the array may comprise a probe for the full mRNA of the nucleic acid sequence of interest. Similarly, in a PCR reaction, the primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art. Methods of extracting RNA from a biological sample are known in the art.

The level of expression may or may not be normalized to the level of a control nucleic acid. Such a control nucleic acid should not specifically hybridize with the GRIN2B nucleotide sequence. This allows comparisons between assays that are performed on different occasions.

ii. GRIN2B Protein Expression

In another embodiment, GRIN2B protein expression may be measured to identify a compound that increased GRIN2B expression. For example, when GRIN2B protein expression is increased in the presence of a compound relative to an untreated control, the compound increased GRIN2B. In a specific embodiment, GRIN2B protein expression may be measured using immunoblot.

Methods for assessing an amount of protein expression are well known in the art, and all suitable methods for assessing an amount of protein expression known to one of skill in the art are contemplated within the scope of the invention. Non-limiting examples of suitable methods to assess an amount of protein expression may include epitope binding agent-based methods and mass spectrometry based methods.

In some embodiments, the method to assess an amount of protein expression is mass spectrometry. By exploiting the intrinsic properties of mass and charge, mass spectrometry (MS) can resolve and confidently identify a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can use mass spectrometry to look for the level of protein encoded from a target nucleic acid of the invention.

In some embodiments, the method to assess an amount of protein expression is an epitope binding agent-based method. As used herein, the term "epitope binding agent" refers to an antibody, an aptamer, a nucleic acid, an oligonucleic acid, an amino acid, a peptide, a polypeptide, a protein, a lipid, a metabolite, a small molecule, or a fragment thereof that recognizes and is capable of binding to a target gene protein. Nucleic acids may include RNA, DNA, and naturally occurring or synthetically created derivative.

As used herein, the term "antibody" generally means a polypeptide or protein that recognizes and can bind to an epitope of an antigen. An antibody, as used herein, may be a complete antibody as understood in the art, i.e., consisting of two heavy chains and two light chains, or may be any antibody-like molecule that has an antigen binding region, and includes, but is not limited to, antibody fragments such as Fab', Fab, F(ab')2, single domain antibodies, Fv, and single chain Fv. The term antibody also refers to a polyclonal antibody, a monoclonal antibody, a chimeric antibody and a humanized antibody. The techniques for preparing and using various antibody-based constructs and fragments are well known in the art. Means for preparing and characterizing antibodies are also well known in the art (See, e.g. Antibodies: A Laboratory Manual, Cold Spring Harbor Laboratory, 1988; herein incorporated by reference in its entirety).

As used herein, the term "aptamer" refers to a polynucleotide, generally a RNA or DNA that has a useful biological activity in terms of biochemical activity, molecular recognition or binding attributes. Usually, an aptamer has a molecular activity such as binging to a target molecule at a specific epitope (region). It is generally accepted that an aptamer, which is specific in it binding to a polypeptide, may be synthesized and/or identified by in vitro evolution methods. Means for preparing and characterizing aptamers, including by in vitro evolution methods, are well known in the art (See, e.g. U.S. Pat. No. 7,939,313; herein incorporated by reference in its entirety).

In general, an epitope binding agent-based method of assessing an amount of protein expression comprises contacting a sample comprising a polypeptide with an epitope binding agent specific for the polypeptide under conditions effective to allow for formation of a complex between the epitope binding agent and the polypeptide. Epitope binding agent-based methods may occur in solution, or the epitope binding agent or sample may be immobilized on a solid surface. Non-limiting examples of suitable surfaces include microtitre plates, test tubes, beads, resins, and other polymers.

An epitope binding agent may be attached to the substrate in a wide variety of ways, as will be appreciated by those in the art. The epitope binding agent may either be synthesized first, with subsequent attachment to the substrate, or may be directly synthesized on the substrate. The substrate and the epitope binding agent may be derivatized with chemical functional groups for subsequent attachment of the two. For example, the substrate may be derivatized with a chemical functional group including, but not limited to, amino groups, carboxyl groups, oxo groups or thiol groups. Using these functional groups, the epitope binding agent may be attached directly using the functional groups or indirectly using linkers.

The epitope binding agent may also be attached to the substrate non-covalently. For example, a biotinylated epitope binding agent may be prepared, which may bind to surfaces covalently coated with streptavidin, resulting in attachment. Alternatively, an epitope binding agent may be synthesized on the surface using techniques such as photopolymerization and photolithography. Additional methods of attaching epitope binding agents to solid surfaces and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, both of which are hereby incorporated by reference in their entirety).

Contacting the sample with an epitope binding agent under effective conditions for a period of time sufficient to allow formation of a complex generally involves adding the epitope binding agent composition to the sample and incubating the mixture for a period of time long enough for the epitope binding agent to bind to any antigen present. After this time, the complex will be washed and the complex may be detected by any method well known in the art. Methods of detecting the epitope binding agent-polypeptide complex are generally based on the detection of a label or marker. The term "label", as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, Ni2+, Flag tags, myc tags, heavy metals, and enzymes (including alkaline phosphatase, peroxidase, and luciferase). Methods of detecting an epitope binding agent-polypeptide complex based on the detection of a label or marker are well known in the art.

In some embodiments, an epitope binding agent-based method is an immunoassay. Immunoassays can be run in a number of different formats. Generally speaking, immunoassays can be divided into two categories: competitive immmunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In some embodiments, the epitope binding agent-based method is an ELISA. In other embodiments, the epitope binding agent-based method is a radioimmunoassay. In still other embodiments, the epitope binding agent-based method is an immunoblot or Western blot. In alternative embodiments, the epitope binding agent-based method is an array. In another embodiment, the epitope binding agent-based method is flow cytometry. In different embodiments, the epitope binding agent-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

iii. GRIN2B Protein Activity

In an embodiment, GRIN2B activity may be measured to identify a compound that increases expression of GRIN2B. GRIN2B is involved in the efficiency of synaptic transmission. Accordingly, neuron firing may be measured as an indication of GRIN2B activity. Neuron signal transmission may be measured using methods standard in the art. For example, when neuron signal transmission is increased in the presence of a compound relative to an untreated control, the compound increases GRIN2B.

In another embodiment, immunoblots may be performed against proteins known to interact with GRIN2B. Increased complexes of GRIN2B and the interacting protein may indicate an increase in GRIN2B. Non-limiting examples of protein known to interact with GRIN2B include actinin, alpha 2, DLG2, DLG3, DLG4, EXOC4, KLOTHO, LIN7B, PSD-95, and RICS as well as other NMDA receptor subunits.

iv. Classification of DNA Sequence to Determine Efficacy for Treatment Using Composition and to Determine Candidates for Such Treatment Compositions which act on NMDA receptors, for example by targeting the GRIN2B nucleic acid sequence, can be used to promote cognitive function. For example, memantine has been used as a drug for Alzheimer's disease.

Memantine acts on NMDA receptors, targeting the GRIN2B subunit. Other molecules that activate NMDA receptors, such as the known co-agonists glycine and D-serine, can then activate GRIN2B gene expression. The GRIN2B gene nucleic acid sequences can thus be used in predicting responses of a drug. As such, the GRIN2B nucleic acid sequences can be used to determine whether a drug will be effective and, subsequently, to determine candidates for treatment using the composition. By classifying DNA sequences to determine whether the candidate has the A allele, comparative amounts of GRIN2B expression in a candidate individual can be determined. The composition can then be used if applicable.

In at least one embodiment, the efficacy or response of a drug can be determined using in vitro methods. For example, cells can be screened for the drug or composition using GRIN2B nucleic acid sequences as a response. Presence of the A allele in the nucleic acid sequences fused to a reporter gene such as an enzyme like lacZ (beta-galactosidase), or a fluorescent protein (green fluorescent protein or red fluorescent protein) can be measured by but limited to histochemical staining, protein blots, liquid scintillation, spectrophotometry, luminometry, or chemiluminescence). In another example, cell viability using but limited to assays that measure cytolysis (lactate dehydrogenase), dye exclusion (Trypan Blue), or mitochondrial activity by an endogenous oxidoreductase enzyme that reduces a tetrazole to a formazan (MTT assay) that can be measured spectrophotometrically to determine drug response or efficacy.

v. Components of the Composition

The present disclosure also provides pharmaceutical compositions. The pharmaceutical composition comprises a compound that increases GRIN2B expression or activity, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a compound that increases GRIN2B expression or activity is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a compound that increases GRIN2B expression or activity in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, a compound that increases GRIN2B expression or activity may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a compound that increases GRIN2B expression or activity (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. A compound that increases GRIN2B expression or activity may be encapsulated in a microemulsion by any method generally known in the art.

In yet another embodiment, a compound that increases GRIN2B expression or activity may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

(b) Administration

In certain aspects, a therapeutically effective amount of a composition of the invention may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

For therapeutic applications, a therapeutically effective amount of a composition of the invention is administered to a subject. A "therapeutically effective amount" is an amount of the therapeutic composition sufficient to produce a measurable response (e.g., enhanced memory performance, reduced memory loss, an improvement in symptoms associated with cognitive decline, or an improvement in symptoms associated with dementia). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, the cognitive decline, the dementia, the symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the time of determining the presence or absence of the A allele. Treatment could begin at a later time after determining the presence or absence of the A allele. Duration of treatment could range from a single dose administered on a one-time basis to a life-long course of therapeutic treatments.

Typical dosage levels can be determined and optimized using standard clinical techniques and will be dependent on the mode of administration.

In addition to the composition comprising a compound that increases GRIN2B activity or expression, standard treatments for memory decline, cognitive decline and/or dementia may be administered. Non-limiting examples of treatment for memory decline, cognitive decline and/or dementia include drugs to boost neurotransmitter levels (e.g., Aricept, Razadyne and Exelon), drugs to regulated the activity of the neurotransmitter glutamate (e.g., memantine), occupational therapy, environmental approaches (e.g., reduce clutter and/or noise), donepezil, vitamin E, diet and exercise, and cognitive rehabilitation.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. Introduction to the Examples.

The earliest and the most severe memory loss in old age and dementia occurs in recent memory and working memory. Compared to young adults, older adults exhibit deficits in working memory, an online memory mechanism that allows manipulation of a current target image amongst distracting stimuli. Remote memory or long-term is better retained. Evidence from neuropsychological and neuroimaging studies of visual working memory indicates that working memory relies on activation of the ventral temporal cortex, and top-down feedback from the prefrontal and medial temporal cortex, and the hippocampus. It has been observed that there are significant individual differences in cognitive aging among healthy cognitively intact older adults due to genetic, learning and environmental factors. Since genetic factors influence working memory performance in the aging brain and the exact underlying mechanisms are not well understood, the present study investigates the variation of a functional promoter polymorphism critical to molecular foundation of learning and memory in individuals' brain processing speed and cortical responses during a working memory task.

The N-methyl-D-aspartate (NMDA) receptors are a class of ionotropic glutamate receptors known to play important roles in cellular and molecular mechanisms associated with efficiency of synaptic transmission during memory. The present study tested the hypothesis that a single nucleotide polymorphism (SNP) within the promoter of the GRIN2B gene (rs3764030 G>A) was functional and that function-guided genotypes could be used to predict brain responses and memory performance (reaction times and accuracy) during working memory. The influence of sequence polymorphisms potentially affecting expression of NMDAR subunits on brain function was determined.

E-twenty-six (ETS) transcription factors are a large class of evolutionarily related, DNA binding proteins. They are characterized by a DNA binding domain that targets a core DNA sequence having a core sequence of 5'-GGA(A/T)-3'. In humans, there are 28 known members of the ETS family, which has been subdivided into 12 different subgroups. In addition to the core sequence, it is thought that flanking sequences contribute to binding specificity of ETS family proteins. Using a genome wide approach, evidence for DNA sequence selectivity of among ETS protein family members has been determined. Other genome wide studies have combined chromatin immunoprecipitation with microarrays or massively parallel sequence analysis.

A potential ETS transcription factor binding site created by a G>A single nucleotide polymorphism (SNP rs3764030) that is 310 bps upstream of the transcription start site for the human GRIN2B gene promoter was identified (FIG. 1). Here, an association of a gain-of-function SNP in the GRIN2B gene and memory performance in a normally aged population of adults is described. A function-guided approach was used to analyze genotype groups based on the observation that the A allele of rs3764030 creates a possible ETS core binding site. In vitro and in vivo data supporting a functional role for this sequence variant is provided.

Brain processing speed reduces over aging brain. It was predicted that variations in GRIN2B may partially count for individual differences in reaction times during active short-term memory retrieval. In addition, neuroimaging studies have shown increased activation within bilateral dorsal lateral prefontal cortices (DPFC) during a working memory task. The cognitive processes become less modular with age, to provide functional compensation in the elderly. It is expected that the GRIN2B gene altered binding of a transcription factor influences cortical responses during memory retrieval.

Example 1

The A Allele of rs3764030 Creates an in vitro DNA Binding Site

Figure 2:
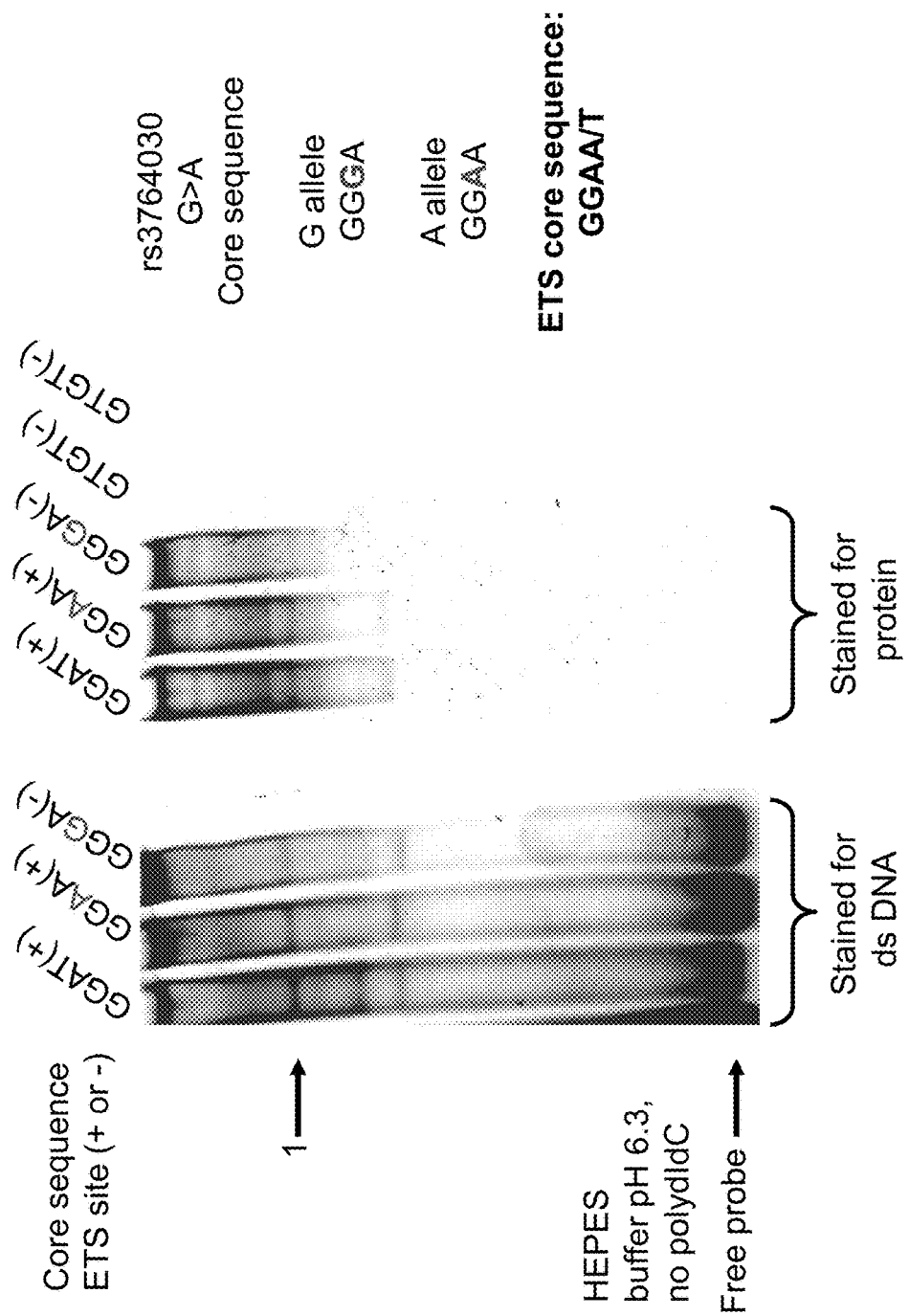
FIG. 2 depicts binding of recombinant Elk-1 protein (an ETS transcription factor) to double stranded DNAs containing the single nucleotide polymorphism (SNP) rs3764030 variant A allele from the human GRIN2B gene promoter. Double-stranded DNA targets (Methods) were sequentially incubated with 1 µg recombinant human Elk-1 protein in EMSA buffer, then incubated with the Elk-1 antibody 20 minutes. DNA-protein complexes were Samples were electrophoresed through 6% polyacrylamide gels in HEPES buffer pH 6.3, without polydIdC. The gel was then stained with the SYBR Green to visualize DNA and SYPRO Ruby for protein bound to DNA. The stained gel was scanned using G:BOX (Syngene, US) for imaging. Elk-1 bound to DNA is indicated by the arrow.

The hypothesis that a SNP (rs rs3764030, G>A) within the promoter of the human GRIN2B gene alters binding of E-twenty six (ETS) family transcription factors was tested. An in vitro DNA binding assay was developed using purified Elk-1, an ETS protein family member that is expressed in brain and DNA targets having either a consensus ETS core binding site (GGAA/T) or DNA targets based on the presence of the ETS binding site from the human GRIN2B gene promoter (GGAA, A allele) or absence of the ETS core binding site (GGGA, G allele). The results in FIG. 2 show that the A allele DNA probe bound recombinant Elk-1 to a greater extent than the G allele DNA probe. When the same gel was stained for protein, it was readily apparent that the A allele DNA probe had more protein associated with it than the G allele DNA probe (FIG. 2).

Example 2

Figure 3:
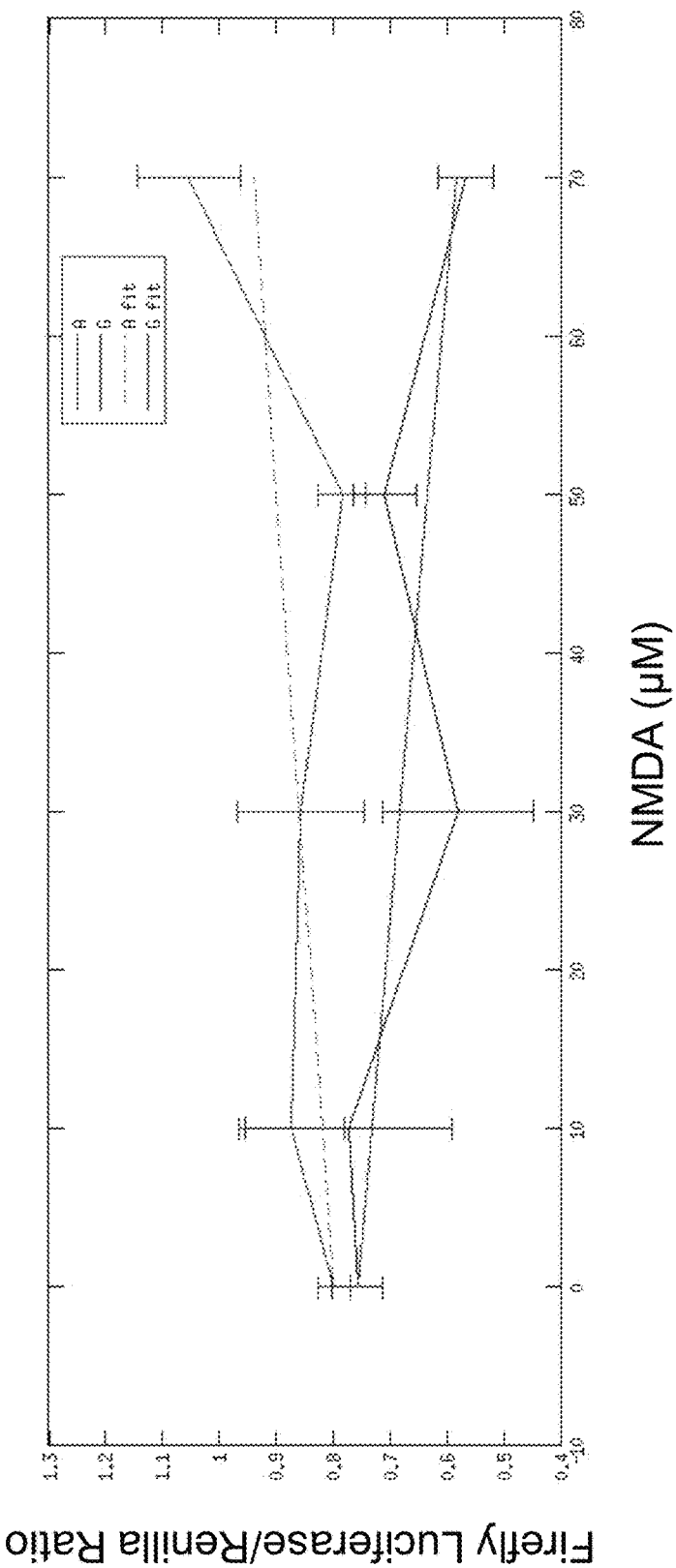
FIG. 3 depicts a concentration dependent response of human GRIN2B promoter in N2a cells carrying either the A or G alleles of SNP rs3764030 to NMDA. Luciferase reporter gene plasmids were constructed in pGL 4.10 (to produce Firefly luciferase, Promega, US). Luciferase reporter plasmids and the pGL4.75 plasmid (to produce Renilla luciferase as a reference) were co-transfected into retinoic acid differentiated N2a cells and assayed for (Methods). After 24 hours of transfection, the cells were incubated for six hours with 0, 30, 50, 70 or 90 µM NMDA for transcription factors binding and then replaced with complete media (with 10% FBS) and cultured for an additional 40-44 hrs. Data are presented as means±SE.

The A Allele of rs3764030 has Greater Basal GRIN2B Reporter Gene Activity than the G Allele in Reporter Gene Assays A reporter gene experiment was performed to determine if the A allele of rs3764030 was functional under activity-dependent conditions. Neuron-like murine neuroblastoma N2A cells were transfected with each of the Elk-1 binding site variants and subsequently treated for four hours with increasing concentrations of NMDA. Six hours later, luciferase activity was measured. A dose-dependent increase in luciferase activity from 2.4-11.5-fold was seen for the A allele (FIG. 3). N2A cells transfected with the G allele luciferase reporter plasmid did not respond to NMDA treatment. These data support the idea that the A allele produces a gain-of-function phenotype.

Example 3

Association of rs3764030 Genotype with Learning Performance

Figure 4A:
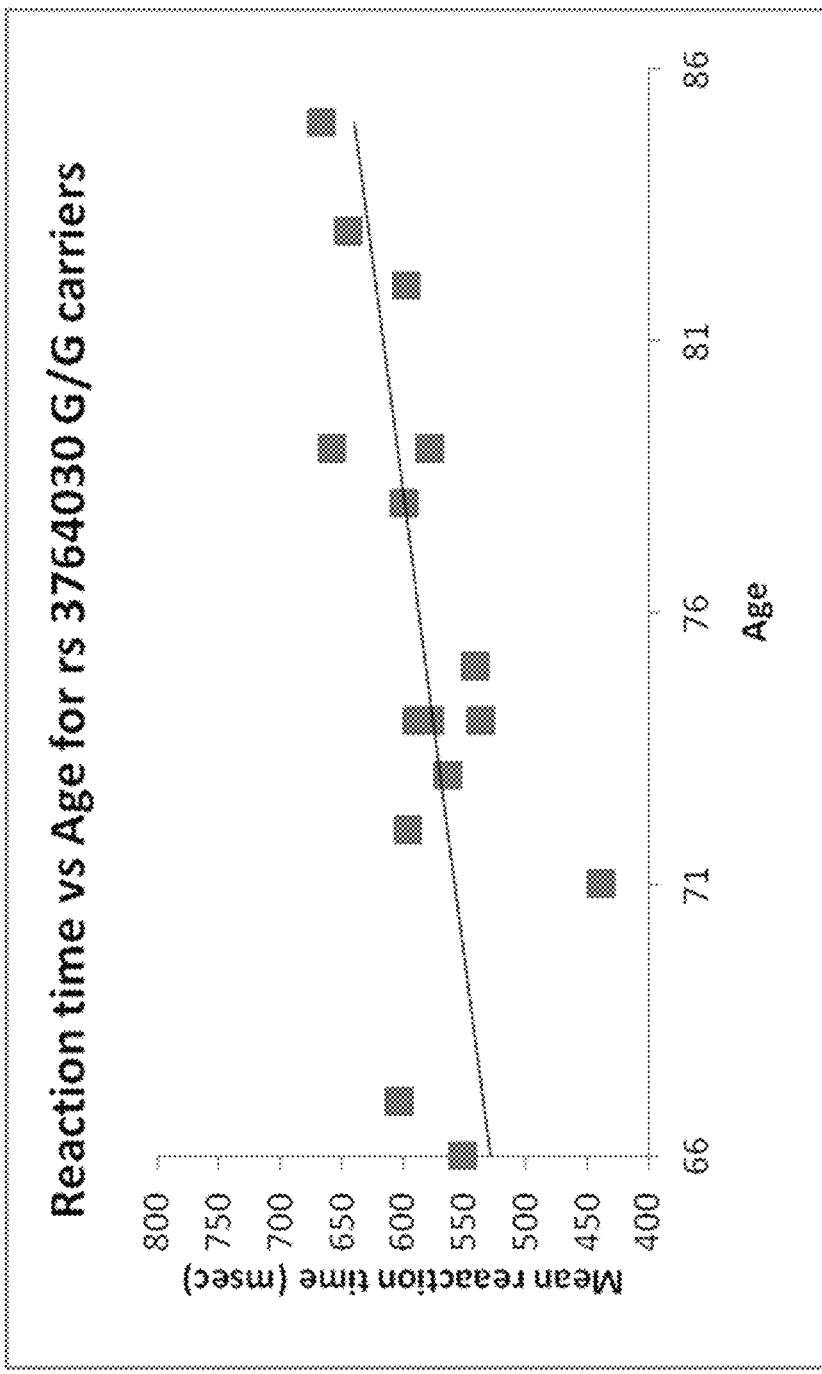
FIG. 4A and FIG. 4B depict graphs showing the mean reaction time with increasing age. Data was examined by analysis of covariance (ANCOVA), based on stratification by A allele carrier genotype group differences. Performance as mean reaction time versus age in GG homozygotes is shown in FIG. 4A, while mean reaction time versus age in A allele carriers (AA and AG genotypes combined) is shown in FIG. 4B. A significant difference in the slopes of the regression lines was observed (−3.994±SE 3.460 for A allele carriers vs 5.848±SE 2.281 for G/G; P=0.026).

Using the functional data from and in vivo reporter gene experiments and in vitro DNA binding experiments, rs3764030 high expression genotypes (A/A, A/G or A allele carriers) and low expression (G/G) genotypes were functionally grouped. This function-based genotype stratification was used to test for association with behavioral performance during memory tests in the study population. Mean reaction time (±SD) was not significantly different between A allele carriers and the G/G genotype group (583.9 msec±81.09 vs 583.2 msec±53.9; P=0.490, by two-tailed test). However, when mean reaction time was analyzed based on age by analysis of covariance (ANCOVA), genotype group differences became apparent. Performance as mean reaction time versus age is shown in FIG. 4A, for G/G carriers, and FIG. 4B, for A allele carriers (A/G+A/A genotypes). A significant difference in the slopes of the regression lines was observed (−3.994±SE 3.460 for A allele carriers vs 5.848±SE 2.281 for G/G; P=0.026).

In another measure, the presence of the A allele was not associated with differences in learning rate within the study population (85.96±65.35 for GG; 65.35±40.40 for A allele carriers; P=0.165). When analyzed by ANCOVA based on age, individuals carrying the A allele had slightly reduced performance with increased age (Slope=−0.217±SE 1.823) while the learning rate among G/G individuals decreased more rapidly with increased age (Slope=−2.276±SE 1.641) However, the difference in the slopes of the two regression lines did not reach significance (P=0.409)(data not shown).

Figure 4B:
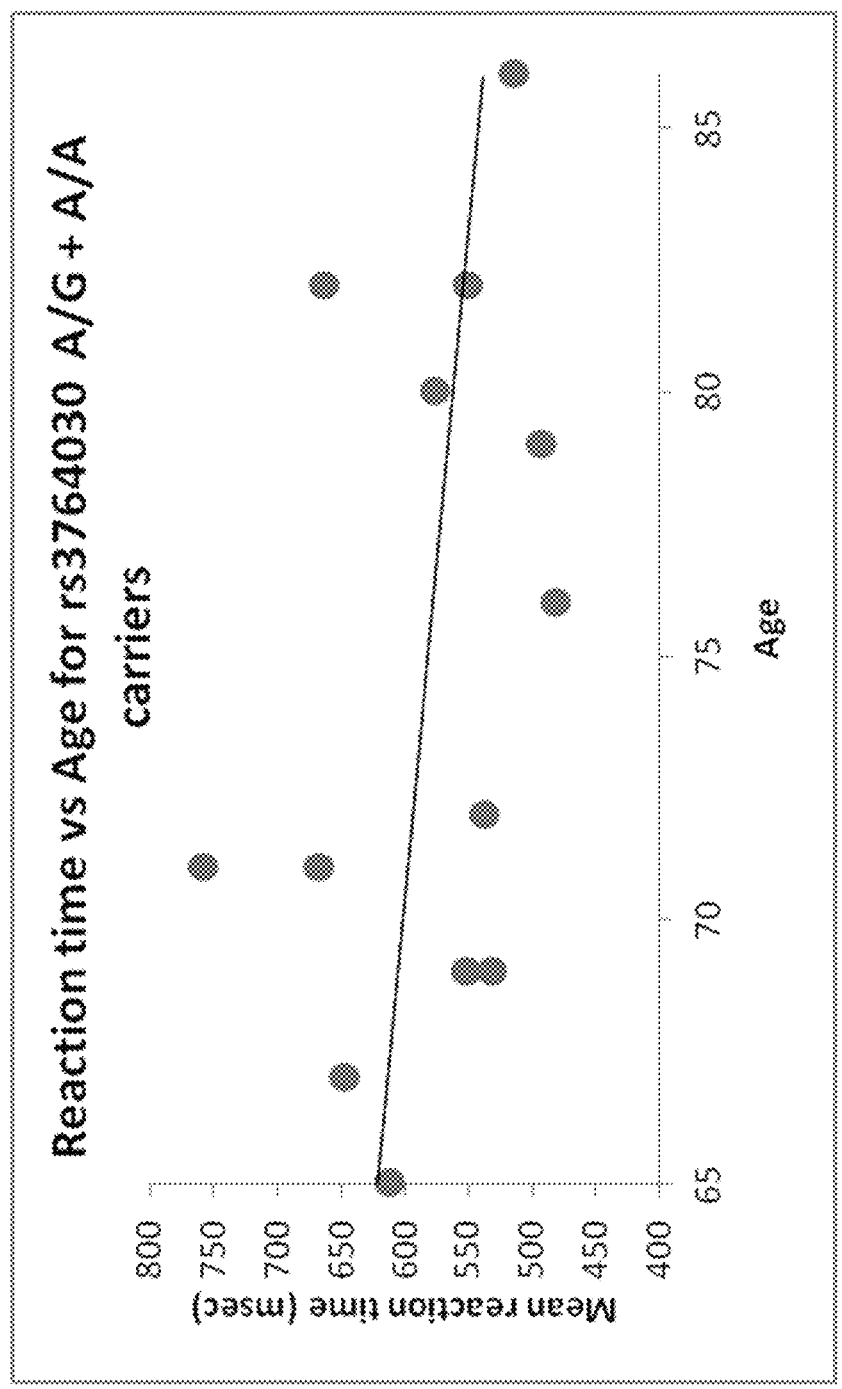
Figure 5A:
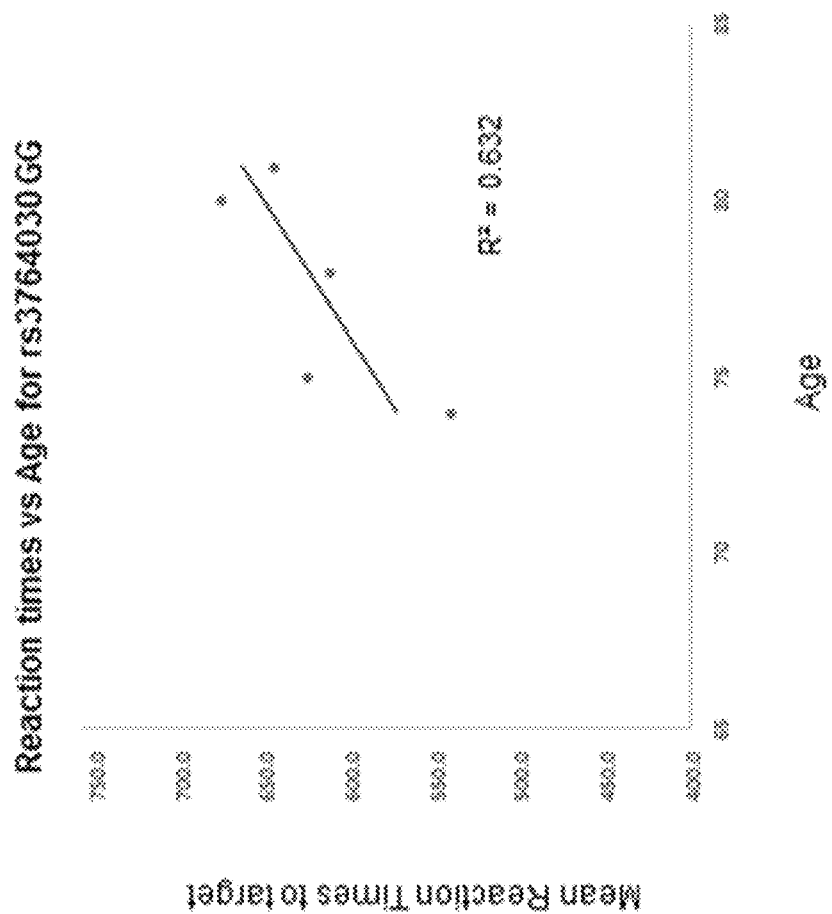
FIGS. 5A and 5B depict graphs showing the mean reaction time with increasing age. Data was examined by analysis of covariance (ANCOVA), based on stratification by A allele carrier genotype group differences. Performance as mean reaction time versus age in GG homozygotes is shown in FIG. 5A, while mean reaction time versus age in A allele carriers (AA and AG genotypes combined) is shown in FIG. 5B. The slopes of the regression lines were significantly different. For A allele carriers as in FIG. 5B, the slope is −3.58±SE 0.21, versus GG genotype as in FIG. 5A having a slope of 13.1±SE 0.20, t(8)=58.5, p<0.001).
Figure 5B:
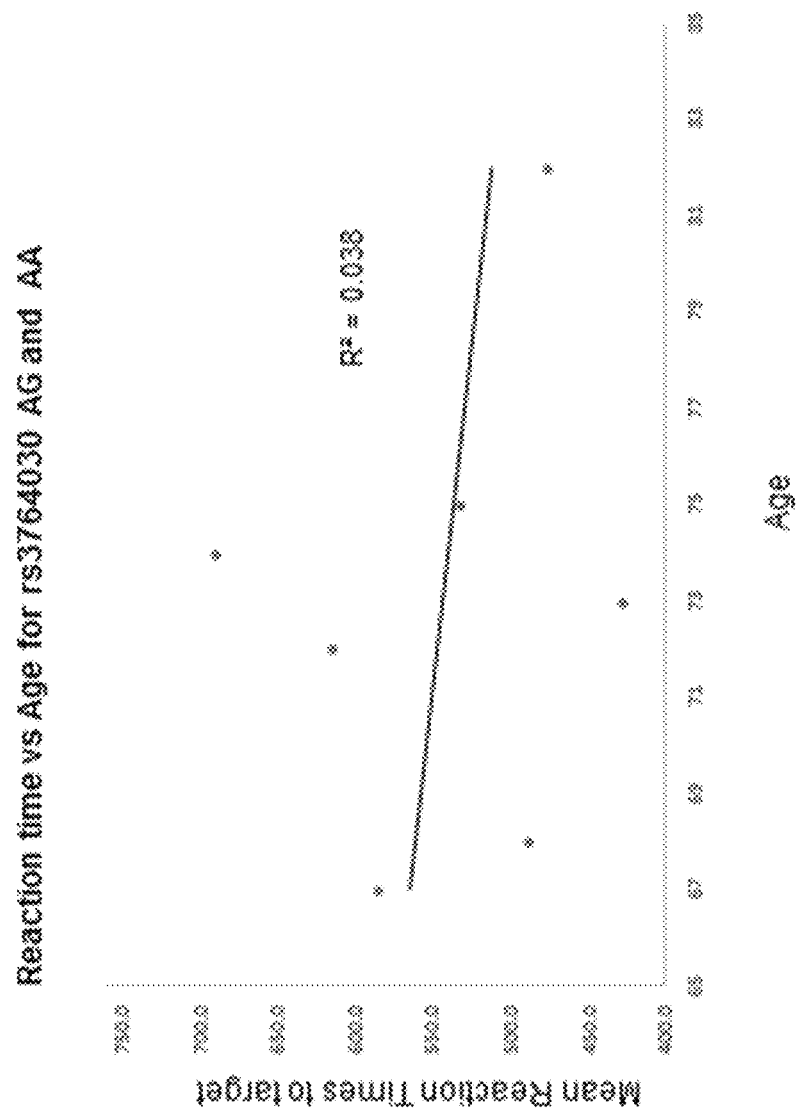

To further validate the results shown in FIGS. 4A and 4B, a second experiment was conducted with a second, separate group of cognitively normal aging subjects. As shown in FIG. 5A, GG carriers had a positive correlation between age and reaction times of repeated memory target match. In contrast, as shown in FIG. 5B, A allele carriers (AA and AG genotypes) did not show such trend; the A allele carriers reactions times decreased slightly with age. The slopes of the regression lines were significantly different. For A allele carriers as in FIG. 5B, the slope is −3.58±SE 0.21, versus GG genotype as in FIG. 5A having a slope of 13.1±SE 0.20, t(8)=58.5, p<0.001). Although the number of individuals tested is small, the differences in performance stratified by the presence of or absence of the A allele are statistically significant. The results are consistent with those presented in the experiment as shown in FIGS. 4A and 4B above, and is a critical validation step for predicting performance of an aging subject.

Example 4

Brain Activation Underlying Working Memory and its Relationship with GRIN2B

Both groups utilized some common cortical areas: frontal (BA areas 6, 9, 10, & 8) and visual cortices, which include fusiform, parahippocampus/hippocampus, middle temporal, precuneus, cingulate, and occipital regions (p<0.001). During working memory task, both groups responded equally in BOLD responses to matches (new or studied target objects). However, they differed in fMRI responses to objects that were mismatched to the target objects held in working memory. Specifically, GG group showed significantly stronger fMRI responses in left inferior temporal (fusiform, L BA area 37; (1.36% signal change) responses to new nonmatch objects (p<0.01 corrected) than that of AG/AA group (1.08% change). The GG group's medial frontal region (BA6, 32) also responded stronger to studied nonmatches than that of AG/AA group (GG=1.48% vs. AG/AA=1.08%; p<0.01).

The mid-frontal regions (L BA 46/9) showed the same pattern, with the GG group (averaged 1.30% signal change) having enhanced fMRI responses versus the AG/AA group (1.15%, p <0.05).

Discussion for the Examples

Luciferase assays indicated that the A allele responded to NMDA receptor activation in a dose-dependent manner and that reporter gene activity under these conditions was significantly higher (2-fold) than cells carrying the same reporter gene but with the G allele. Results from gel shift experiments indicated that the A allele could create a functional binding site for at least one ETS domain transcription factor. Behavioral results showed that presence of the A allele was not associated with differences in either memory accuracy (97% for GG; 96% for AG/AA) or reaction times (584 ms and 589 ms). However, A allele carriers showed decreased reaction time with age (meaning better memory performance) compared with the GG genotype (p=0.026 based on difference in slope of the regression line between GG and AG=AA groups) in a group of cognitively normal aged adults. This finding was replicated in a second cohort of cognitively normal subjects. A allele carriers performed better compared with GG genotype individuals (p<0.001) Brain imaging results revealed that alterations of brain responses in ventral temporal, and in prefrontal cortices are associated with the changes in subunit of NMDA receptors, which confirms level of facilitation in memory functions.

In this study, a biological effect of the GRIN2B promoter SNP, rs3764030 G>A, was determined, showing that the A allele in transfected N2a cells, responded to NMDA agonism (NMDA receptor activation) in a dose-dependent manner relative to the common G allele. In addition, it was shown that the A allele was capable of binding the ETS transcription factor, Elk-1, in vitro. These observations were the mechanistic basis for providing the support for a gain-of-function gene variant and for combining genotype groups (A allele carriers vs non-carriers) for subsequent genetic association studies. The cohort recruited in this study was composed of cognitively normal older adults. Better performance in reaction time to a learning test in A allele carriers was determined.

This study is the first report of a SNP that affects GRN2B mRNA levels. The knowledge of a functional polymorphism that may increase levels of GRIN2B mRNA and possibly GluN2B subunits suggests a mechanism for protecting the brain from age-related cognitive decline.

The results from the gel shift experiment indicated that the A allele created a functional binding site for at least one ETS domain transcription factor. The ETS domain transcription factor family has 27 known members that are expressed by different human cells. The initial focus was on Elk-1 because its expression profile in different tissues includes the brain.

Conclusions. These results support the idea that presence of the A allele of rs3764030 positively influenced reaction time. Alternatively, individuals with the G allele, while having slower responses with increasing age, may have had a stronger capability to suppress distractors. Either interpretation is consistent with the idea that changes in subunit stoichiometry of NMDA receptors confer distinct functional properties of memory functions. The grouping of A allele-genotypes for association analyses was justified based on reporter gene assays and gain-of-function ETS transcription factor binding to DNA. Future longitudinal follow-up of the subjects will bring insights of whether the gene variation might be a potential indicator for cognitive reserve or risk-factor for old-age dementia.

Methods for the Examples.

Participants: Twenty-eight right-handed older adults (ages 65-86) were recruited as a cohort to participate in the experiment. Individuals were cognitively normal with no diagnosis of dementia, substance abuse, major psychiatric illness, or other illnesses or conditions affecting the central nervous system, such as meningitis or traumatic brain injury. Written consent forms were obtained from each of the participants.

Genotyping: Subjects were genotyped for the rs3764030 G>A GRIN2B promoter SNP using a 5' exonuclease assay. Genotypes were independently confirmed using direct sequence analysis with no discrepancies. Genotype frequencies met Hardy-Weinberg expectations in the study population. For association analyses, subjects were grouped based on presence of A allele (GG genotype versus GA and AA genotypes). Both GG (n=15) and AG/AA (n=13) groups were well matched in age (mean age 75.5 for GG, 74.5 for AG/AA), gender (9 female and 8 female respectively). Both genotype groups had high cognitive functioning with comparable scores on the Mini-Mental State Exam (mean=29).

Experimental paradigm: Study Phase. Participants were initially instructed to study and memorize 60 line drawings individually displayed in a computer task, cycling through each by pressing the spacebar to move onto the next stimulus. This phase lasted approximately 10 minutes per subject. After these two study phases, each participant was asked to complete a recognition task during which they identified the pictures presented as "memorized" or "not memorized" by pressing the corresponding keyboard button (placement of the keys was counterbalanced). Participants subsequently performed a recognition test that included 60 studied and 60 new objects (mean accuracy=98.2%).

Stimuli. Stimuli consisted of 120 black and white line-drawings of common objects developed by Snodgrass & Vanderwart (1980). Pictures were presented within a rectangular area of 8.3 cm by 5.8 cm and displayed in front of a black background. The visual display and responses were controlled by E-Prime presentation software (Psychology Software Tools, Pittsburgh, Pa.). The computer screen was approximately 65 cm from participants with a visual angle of about 7 degrees. The target pictures, at the beginning of each trials, were demarcated by a 6.5 mm green border as indication of the item to be held in mind as Of the 120 pictures, 40 were used as studied distracters, while the other 80 were new objects that had not been previously studied (40 new distracters; 40 new targets). Test objects were classified into one of three groups: (a) studied targets, (b) studied distracters, or (c) new distracters. All target objects were new but distracter objects included both studied and new objects.

Test Phase. Participants then performed the working memory task using a button held in each hand. Assignment of hands was counterbalanced across subjects. For each working memory trial, participants were shown a sample object to hold in mind and were asked to indicate whether the following nine test objects were the same or different from the target. Participants then performed a Delayed Match to Sample (DMS) task consisted of 40 trials separated into 4 blocks of 10 trials each. Each trial began with the presentation of a sample target object for 2000 msec and was distinguished by a green border. The sample target object was followed (ISI=700±100 msec) by 10 successive test objects with a stimulus duration of 2000 msec (ISI=500±200 msec). Each trial lasted 27.5 seconds.

The test portion of each trial contained a pseudo-random presentation of target and distracter objects where the target object, a studied distracter, and a new distracter were presented three times each, resulting in nine of the ten test items in a trial. One additional 'filler' object was included in each trial to reduce the potential for subject expectancy and served either as a $4^{th}$ target (16.7% of trials), $4^{th}$ studied distracter (16.7% of trials), $4^{th}$ new distracter (16.7% of trials), or a new distracter never previously shown (50% of trials). None of the objects, whether serving as a target or distracter, were used in any subsequent trials. Across trials, stimuli from the three experimental conditions were equally distributed across all 10 serial positions. FIG. 1 illustrates the distribution of objects in relation to repetition across the 10 serial test object positions.

Participants were told to hold the sample target object in mind and indicate whether the following 10 test objects were the same or different from the sample target. Assignment of hands to indicate a target versus distracter object was counterbalanced across subjects. Subjects were also instructed to forget the previous sample target object only when a new sample target object appeared.

Reaction times and accuracy of behavioral responses were recorded as msecs and number of correct responses.

Behavioral data analysis: Behavioral data, i.e. accuracy and reaction times, were calculated to each of the memory retrieval, new or studied memory matching target, new or studied nonmtach distractors. Please see Caggiano, Jiang, Parasurman, 2006 for detailed description.

Event-related functional MRI Acquisition and Analysis: The healthy normal older adults were scanned inside of a 3 Tesla Siemens Trio MRI scanner at the University of Kentucky. High-resolution whole brain structural MRI was obtained for each subject. Twenty-two slices whole brain T2* weighted functional images were obtained every 2.5 seconds for each of the eight series. [T2*-weighted EPI (64×64 matrix, 2.5 sec RT, whole brain, 3.6 mm cubic voxel size]. Images were realigned for head motion correction and fMRI Image volumes were reconstructed using AFNI software (Cox, 1996). Motion was corrected and the slice timing differences were adjusted and intensity normalized to allow for the calculation of activation as a percentage of signal change. General linear models were applied for the multiple regression analysis. The multiple regression models contained orthogonal contrasts of interest and additional regressors of no importance to obtain changes in mean fMRI signals.

Molecular and cellular characterization of a functional GRIN2B SNP: Luciferase vector construction. The rs3764030 SNP within the 1.7 kb 5' flanking region which covered the GRIN2B gene noncoding exon, for example exon 1, and 1530 bps upstream of the human GRIN2B gene transcription start site was PCR amplified and cloned into pGL 4.10 (to produce Firefly luciferase, Promega, US) plasmid for luciferase reporter gene assay. The four plasmid constructs were each designed according to a combination of alleles (either A or G) and the DNA strand transcribed, which included: positive orientation with allele A (A+ plasmid), positive orientation with allele G (G+ plasmid), negative orientation with allele A (A− plasmid) and negative orientation with allele G (G− plasmid). The orientations and alleles in the constructs were confirmed by direct sequencing in ABI 310 genetic sequencer (Applied Biosystems, US).

Cell Culture, Transfection, and Luciferase assay. Murine N2a cells produce functional NMDA receptors (Mantuano et al 2013; Van der Valk and Vijverberg, 1990). The cells were maintained in RPMI medium supplemented with 5% fetal bovine serum until approximately 80% confluent. Prior to transfection the cultures were transferred into 96 well cell culture plates (Costar #3904, US) 24-48 hours with serum free RPMI medium 1640. The four plasmid constructs were co-transfected with pGL4.75 plasmid (to produce Renilla luciferase as control) for dual-luciferase reporter gene assay (Promega, US) using Lipofextamine-LTX reagent (Life science, US). After 24 hrs of transfection, the cells were activated 4-6 hours with 0, 30, 50, 70 and 90uM NMDA for transcription factors binding and then replaced with completed media (with 10% FBS) to cultured additional 40-44 hrs at 37° C. in 5% CO2. Each NMDA concentration was replicated three times for statistical power. The luciferase activities were then measured in Synergy 4 plate reader (Biotek, US).

Murine Neuro-2a neuroblastoma cells were maintained in RPMI medium 1640 with 10% Fetal Bovine Serum (complete medium) at 37° C. in 5% CO2. Cells were plated in 96 well cell culture plates ($1\times10^6$ cells) with laminin and Poly-L-Ornithine) 24 hrs before neural differentiation. For differentiation, cells were incubated in the presence of 1 µM retinoic acid for 24 hrs in serum-free RPMI medium. The N2a cells were differentiated on 96 well cell culture plate (Costar #3904, US) 24-48 hours with serum free RPMI medium 1640 before transfection. The 4 plasmid constructs were co-transfected with pGL4.75 plasmid (to produce Renilla luciferase as control) for dual-luciferase reporter gene assay (Promega, US) using Lipofextamine-LTX reagent (Life science, US). After 24 hours of transfection, the cells were activated 4-6 hours with 0, 30, 50, 70 and 90 uM NMDA for transcription factors binding and then replaced with completed media (with 10% FBS) to cultured additional 40-44 hours at 37° C. in 5% CO2. Each NMDA concentration was replicated three times for statistical power. The luciferase activities were then measured in Synergy 4 plate reader (Biotek US).

Electrophoretic Mobility Shift Assay (EMSA). To monitor the interaction between the ETS domain transcription factor, Elk-1, and its DNA recognition sequence in vitro, we used EMSA. The DNA sequences for positive control containing a GGAT consensus core binding sequence were: Forward: 5' ACGCTAACCGGATATAACGCTA 3' (SEQ ID NO:2) and Reverse: 5' TAGCGTTATATCCGGTTAGCGT 3' (SEQ ID NO:3). The negative control region was: Forward: 5' ACGCTAAACAGTGTCAACGCTA 3' (SEQ ID NO:4) and Reverse: 5' TAGCGTTGACACTGTTTAGCGT 3' (SEQ ID NO:5), as described in Wei et al (2010). The forward and reverse sequence for GRIN2B A allele which created the ETS binding site were: 5' CATCTCCGGGGAACACGCGAA 3' (SEQ ID NO:6) and 5' TTCGCGTGTTCCCCGGAGATG 3' (SEQ ID NO:7), repectively. The forward and reverse sequences for GRIN2B G allele were 5' CATCTCCGGGGGACACGCGAA 3' (SEQ ID NO:8) and 5' TTCGCGTGTCCCCCGGAGATG 3' (SEQ ID NO:9).

The complementary pairs of DNA oligonucleotides were first annealed in Biorad C1000 thermocycler with 1° C./1 min decreasing from 95° C. to 20° C. The annealing buffer composition was 10 mM Tris-HCl pH 8.0, 1 mM EDTA and 50 mM NaCl. The annealed dsDNA was then incubated with 1 µg recombinant human Elk-1 protein (Sigma Aldrich, US) on ice for 1 hour in EMSA buffer, then incubated with the Elk-1 antibody (SC-355)(Santa Cruz Technology, US) 20 minutes in room temperature. The compositions of EMSA buffer was 50 mM HEPES pH7.5, 10 mM $MgCl_2$, 5% glycerol, 1 mM DTT, 0.3% BSA and 1 mM EDTA. The experiment was conducted in 6% retardation gel (Life Technology, US), running 95 volt for 80 minutes. The gel was then stained with the EMSA SYBR Green and SYPRO Ruby kit (E-33075) (Life technology, US) according to the instruction manual. The stained 6% retardation gel was scanned in G:BOX (Syngene, US) for imaging.

This work was partially funded by grants P30 AG028383 and K01 AG000986 awarded by NIH, the disclosure of which are hereby incorporated by reference in their entirety.

We claim:

1. A method comprising:

a) detecting in an mRNA transcript including a GRIN2B nucleic acid sequence from a biological sample obtained from a human subject the absence of an A allele at SNP rs3764030 using sequencing, hybridization or an amplification technique and b) administering to the human subject without an A allele at SNP rs3764030 a therapeutically effective amount of memantine.

2. The method of claim 1, wherein detecting in the mRNA transcript comprises:

obtaining a biological sample from the human subject.

3. The method of claim 1, wherein the A allele is detected by hybridization of a probe specific to the A allele.

4. The method of claim 3, wherein the probe comprises SEQ ID NO:6 (CATCTCCGGGGAACACGCGAA).

5. The method of claim 1, further comprising determining efficacy of the memantine.

6. The method of claim 1, further comprising determining an amount of expression of the GRIN2B nucleic acid sequence.

7. The method of claim 6, wherein determining the amount of expression includes at least one of arrays, polymerase chain reaction, nuclease protection assays, and Northern blot analyses.

8. The method of claim 1, wherein the amplification techniques include at least one of polymerase chain reaction, ligase chain reaction, nucleic acid sequence based amplification, strand displacement amplification, transcription mediated amplification, loo-mediated isothermal amplification, Q-beta replicase, rolling circle amplification, 3SR, ramification amplification, multiplex ligation-dependent probe amplification, restriction fragment length polymorphism, single strand conformation polymorphism, and denaturing high performance liquid chromatography.

* * * * *

SEQUENCE LISTING

<160> NUMBER OF SEQ ID NOS: 9

<210> SEQ ID NO 1
<211> LENGTH: 1001
<212> TYPE: DNA
<213> ORGANISM: Homo sapiens
<220> FEATURE:
<221> NAME/KEY: misc_feature
<222> LOCATION: (501)..(501)
<223> OTHER INFORMATION: r=a or g

<400> SEQUENCE: 1

| | | | | | |
|---|---|---|---|---|---|
| cgcgtcagtg | tgccccttcc | aagaaatgcc | cagtgtgcac | cccgtgcaca | atcagaaccc | 60 |
| attcagcaca | agcccggggt | gggaggcggc | gctgctgctg | gaggcgatgg | ggagagcgag | 120 |
| cgagacaagt | cagcagcaat | gcagatgggg | ctggggccg | cactcgctgg | cgagttaagt | 180 |
| gggaattgtg | tttctgcgtg | tgtgtgagtg | tgtgttgctg | tatggtgccg | cttctccccc | 240 |
| ccttcctcct | tccttcccac | ttccctcctt | cgctcgctcc | ctccctctct | cctcttccat | 300 |
| tcaggttggc | tttcccacct | ctcatccgtg | cctgtcccag | gaatggtata | gccagacctt | 360 |
| ttctgaatta | tttatagacc | ggtaccagct | gttttcaatt | cctctcgtgt | gcactctgtg | 420 |
| ggaaatgcgg | ggtttcctcc | cccctttcct | taaaacgaat | tgatatcttt | ttcggaatgc | 480 |
| attttctca | ccctccgggg | racacgcgaa | tcaagccctg | accgcctctt | tttcccccctt | 540 |
| aggaagggga | cgctttggga | atgaccatgc | tccaccgagg | gacggagccg | gccccagct | 600 |
| tctccacaca | gagcctcctc | cactaacgct | ccaaaaacca | aaaaccgtaa | ttgccagaag | 660 |
| aagcgttaaa | aatctattcc | agccactaac | ctcacatgca | cacggaataa | ttactctgga | 720 |
| ttctgcattg | tgagctgctc | tccataccct | gaattacctt | tgaattaaat | cttttttttt | 780 |
| ttgaatttgc | atctcttcaa | gacacaagat | taaaacaaaa | tttacgctaa | attggatttt | 840 |
| aaattatctt | ccgttcattt | atccttcgtc | tttcttatgt | ggatatgcaa | gcagaagaa | 900 |
| gggactggac | attcccaaca | tgctcactcc | cttaatctgt | ccgtctagag | gtttggcttc | 960 |
| tacaaaccaa | ggtagggcaa | attctatttt | attttttcct | c | | 1001 |

<210> SEQ ID NO 2
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 2
acgctaaccg gatataacgc ta                                              22

<210> SEQ ID NO 3
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 3
tagcgttata tccggttagc gt                                              22

<210> SEQ ID NO 4
<211> LENGTH: 22
<212> TYPE: DNA
<213> ORGANISM: Artificial Sequence
<220> FEATURE:
<223> OTHER INFORMATION: SYTNEHSIZED

```
<400> SEQUENCE: 4
acgctaaaca gtgtcaacgc ta                                              22

<210> SEQ ID NO 5
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 5
tagcgttgac actgtttagc gt                                              22

<210> SEQ ID NO 6
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 6
catctccggg gaacacgcga a                                               21

<210> SEQ ID NO 7
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 7
ttcgcgtgtt ccccggagat g                                               21

<210> SEQ ID NO 8
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 8
catctccggg ggacacgcga a                                               21

<210> SEQ ID NO 9
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 9
ttcgcgtgtc ccccggagat g                                               21
```